(12) United States Patent
Valpey, III et al.

(10) Patent No.: US 8,158,108 B2
(45) Date of Patent: Apr. 17, 2012

(54) VOC-FREE COMPRESSED GAS AEROSOL COMPOSITIONS

(75) Inventors: Richard S. Valpey, III, Lindenhurst, IL (US); Paul A. Clark, Racine, WI (US); Jessica A. Heiser, Atlanta, GA (US)

(73) Assignee: S.C. Johnson & Son, Inc., Racine, WI (US)

( * ) Notice: Subject to any disclaimer, the term of this patent is extended or adjusted under 35 U.S.C. 154(b) by 1055 days.

(21) Appl. No.: 11/819,378

(22) Filed: Jun. 27, 2007

(65) Prior Publication Data

US 2008/0003185 A1 Jan. 3, 2008

Related U.S. Application Data

(60) Provisional application No. 60/816,870, filed on Jun. 28, 2006.

(51) Int. Cl.
| | |
|---|---|
| A61K 9/12 | (2006.01) |
| A61K 8/00 | (2006.01) |
| A01N 25/00 | (2006.01) |
| A01N 25/02 | (2006.01) |
| C11D 3/50 | (2006.01) |

(52) U.S. Cl. ......... 424/43; 424/405; 424/76.2; 514/919; 510/101; 512/2

(58) Field of Classification Search ............... 424/43, 424/405, 76.2; 514/919; 510/101; 512/2
See application file for complete search history.

(56) References Cited

U.S. PATENT DOCUMENTS

| | | | |
|---|---|---|---|
| 3,829,578 A | 8/1974 | Fleming et al. | |
| 4,382,078 A | 5/1983 | Berkhoff et al. | |
| 5,266,690 A | 11/1993 | McCurry, Jr. et al. | |
| 5,449,763 A | 9/1995 | Wulff et al. | |
| 5,489,433 A | 2/1996 | Aboud | |
| 5,494,912 A | 2/1996 | Halazy et al. | |
| 5,527,803 A | 6/1996 | Halazy et al. | |
| 5,538,978 A | 7/1996 | Halazy et al. | |
| 5,670,475 A | 9/1997 | Trinh et al. | |
| 5,734,029 A | 3/1998 | Wulff et al. | |
| 5,859,218 A | 1/1999 | Wulff et al. | |
| 5,962,399 A | 10/1999 | Wulff et al. | |
| 6,077,318 A | 6/2000 | Trinh et al. | |
| 6,180,088 B1 | 1/2001 | Ohtsubo et al. | |
| 6,238,646 B1 | 5/2001 | Zembrodt | |
| 6,248,135 B1 | 6/2001 | Trinh et al. | |
| 6,451,065 B2 | 9/2002 | Trinh et al. | |
| 6,531,144 B2 | 3/2003 | Kashima et al. | |
| 6,729,559 B2 | 5/2004 | Zanma et al. | |
| 6,861,396 B2 | 3/2005 | Baker et al. | |
| 6,881,757 B2 | 4/2005 | Moodycliffe et al. | |
| 7,147,822 B2 | 12/2006 | Parkhurst et al. | |
| 2003/0005522 A1 | 1/2003 | Trinh et al. | |
| 2003/0035852 A1 | 2/2003 | Pullen | |
| 2003/0092593 A1 | 5/2003 | Farooq et al. | |
| 2004/0037782 A1 | 2/2004 | Hernandez et al. | |
| 2004/0063600 A1 | 4/2004 | Williams et al. | |
| 2004/0067322 A1 | 4/2004 | Baker et al. | |
| 2004/0242428 A1 | 12/2004 | Pullen | |
| 2005/0019309 A1 | 1/2005 | Park et al. | |
| 2005/0089540 A1 | 4/2005 | Uchiyama et al. | |
| 2005/0124512 A1 | 6/2005 | Woo et al. | |
| 2005/0165042 A1 | 7/2005 | Zhang et al. | |
| 2005/0192197 A1 | 9/2005 | Man et al. | |
| 2006/0292111 A1* | 12/2006 | Valpey et al. | 424/76.2 |
| 2007/0194040 A1* | 8/2007 | Tasz et al. | 222/4 |
| 2009/0311195 A1* | 12/2009 | Clark et al. | 424/45 |

FOREIGN PATENT DOCUMENTS

| | | |
|---|---|---|
| EP | 0 488 668 B1 | 4/1997 |
| JP | 06-329510 A | 11/1994 |
| WO | WO 2004/093836 A2 | 11/2004 |
| WO | WO 2004/093836 A3 | 11/2004 |
| WO | WO 2005/005264 A2 | 1/2005 |
| WO | WO 2006/102052 A2 | 9/2006 |
| WO | WO 2007/002778 A1 | 1/2007 |

OTHER PUBLICATIONS

Goldschmidt Personal Care, Degussa, Tagat CH 60, May 2003, pp. 1-5.*

* cited by examiner

*Primary Examiner* — Mina Haghighatian

(57) ABSTRACT

Certain surfactants suitable for use alone to dissolve a water-insoluble component in compositions is described for providing VOC-free compressed gas aerosol compositions. The compositions include water-insoluble component(s), a surfactant and water. The water-insoluble component(s) can be active agent(s), such as fragrance(s) and/or an insecticide(s). The surfactant is present as a single surfactant which, in the absence of a solvent, dissolves or disperses the water-insoluble component(s) and provides a homogenous blend in water which provides a stable compressed gas emulsion. The surfactant is an anionic surfactant or a nonionic surfactant, in particular nonionic alkylpolyglycosides; nonionic cocoglucoside; nonionic alkylene oxide extended chain alkylpolyglycosides; anionic sodium lauryl ether sulfate (SLES), nonionic $C_{13}$-$C_{15}$ oxoalcohol ethoxylate with 8 ethylene oxides (EO), nonionic $C_{12}$-$C_{14}$ secondary alcohol ethoxylate with 7EO or 12EO, polyethylene glycol (PEG) hydrogenated castor oil wherein the PEG is PEG-60 or PEG-40, polyglyceryl-10 laurate and polyglyceryl-6 caprylate.

17 Claims, 1 Drawing Sheet

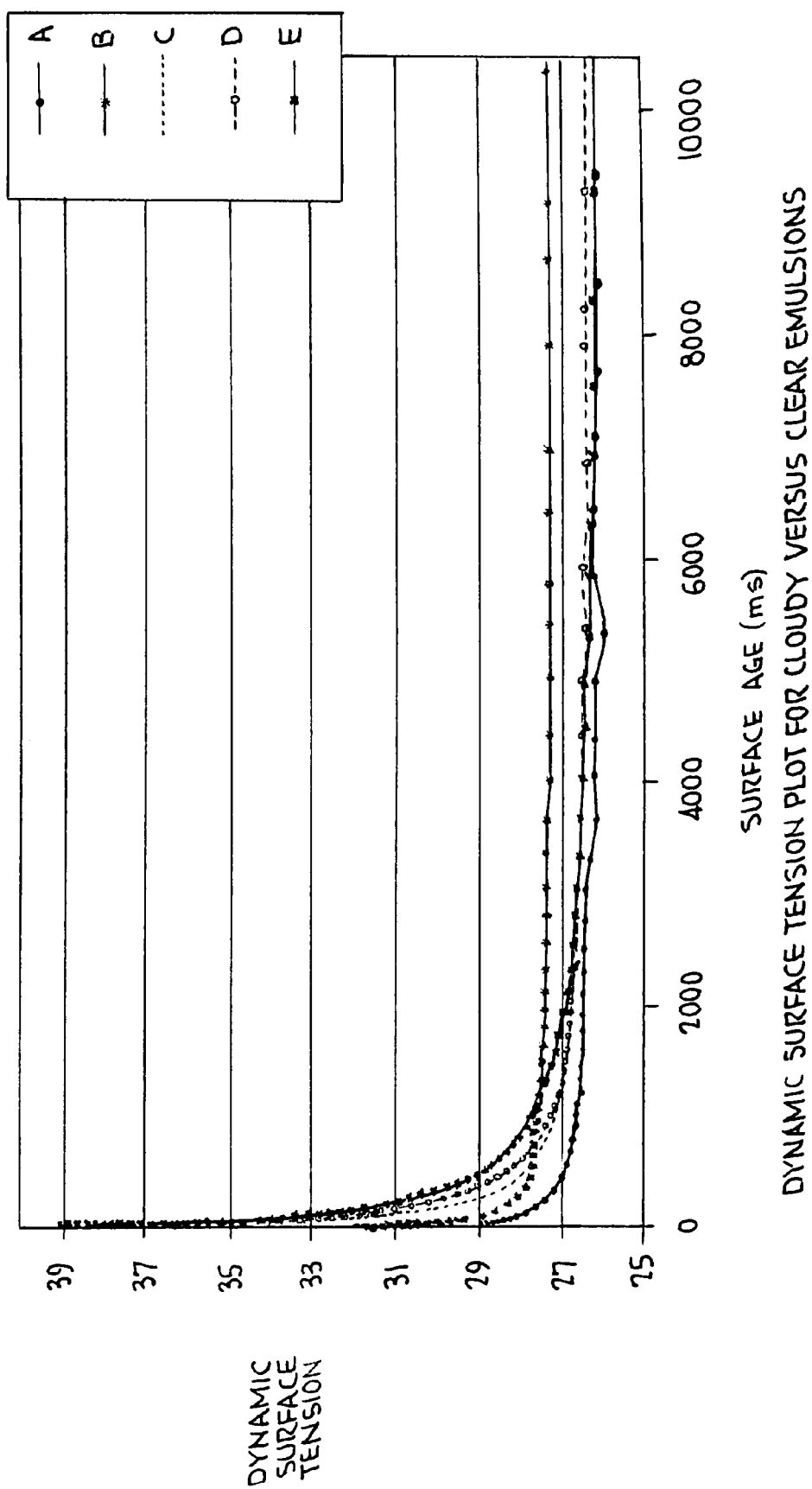

VOC-FREE COMPRESSED GAS AEROSOL COMPOSITIONS

RELATED APPLICATION

This application claims the benefit of U.S. Provisional Patent Application Ser. No. 60/816,870 filed Jun. 28, 2006.

FIELD OF INVENTION

The present invention relates to the inclusion of a single surfactant selected from specified surfactants in various compositions to dissolve or disperse water insoluble components of the compositions to provide VOC-free compressed gas aerosol compositions.

BACKGROUND OF INVENTION

Liquid components or compositions, such as fragrance oils, insecticides, medicines, cleaners, polishes, hair sprays, cosmetics, paints, and the like are composed of materials that are insoluble in water. These liquid components and compositions are used in the manufacture of aerosol compositions. Such liquid components and compositions usually require the inclusion of solvents to produce a homogeneous blend in water.

Further, aerosol compositions are generally pressurized with hydrocarbon propellants. For many reasons, including environmental concerns, industries are replacing hydrocarbons in aerosol compositions with compressed gas. However, compressed gas aerosol compositions have typically had several problems, including, but not limited to, not being able to produce stable aqueous mixtures of oils, insecticides, medicines, cleaners, polishes, hair sprays, and cosmetics. Due to this problem, most compressed gas aerosol compositions produced today contain materials to help dissolve or disperse these "active" ingredients. Typically, these materials are mixtures of surfactant(s), solvent(s) and volatile organic compound(s) (VOC(s)). Alcohols, such as ethanol and isopropyl alcohol, are common solvents used in these compositions. Glycols and their derivatives are also used as solvents in these compositions.

Since fragrance oils, insecticides, cleaners, polishes, hair sprays, cosmetics, and the like are composed of materials that are insoluble in water, solvents have previously been added to such compositions to increase the overall solubility of these materials. The desirability of VOC-free aerosol systems has created a need for stable emulsions not containing solvents.

U.S. Pat. No. 4,382,078 discloses a two-phase water-based aerosol composition including an active ingredient, a surfactant, a stabilizer and dimethylether (DME) propellant. The surfactant is a block copolymer of ethylene oxide and propylene oxide of a specified formula. Perfumes, insecticides, bactericides, fungicides, herbicides or deodorizing agents may be included in the composition.

U.S. Pat. No. 6,238,646 B1 discloses aqueous aerosol compositions for the delivery of atomized oil, such as a fragrance oil, insecticide oil and medicinal oil. The composition includes water, a water-soluble propellant such as dimethylether, dispersed oil phase in water, nonionic surfactant and a polymeric emulsifier. The nonionic surfactant is stated to help suspend the oil particles by decreasing the droplet size of the dispersed phase in the water.

U.S. Patent Application Publication No. 2004/0209795 A1 (which corresponds to WO 2005/093836 A2) discloses a perfume composition in the form of a highly transparent VOC-free microemulsion. The microemulsion includes an oil (such as a perfume oil); a surfactant system including one or more ionic surfactants and one or more nonionic surfactants; a solubilizing aid and water. The oil may contain a solvent. The ionic surfactants can be anionic, cationic or amphoteric. The amount of surfactant system present is stated to be dependent on essentially the amount of oil and solubilizing aid present and the amount necessary to provide a microemulsion. The solubilizing aid can be an organic or inorganic salt, such as selected from the group consisting of ammonium, alkaline and alkaline earth salts of $C_1$ to $C_{15}$ mono- and dicarboxylic acid derivatives, bicarbonates, halogenates, thiocyanates, and mixtures of the salts.

U.S. Patent Application Publication No. 2005/0020698 A1 (which corresponds to WO 2005/005264 A2) discloses an aerosol product without a vapor tap and having a more stable emulsion using a significantly lower ratio of propellant to product. The more stable emulsion is provided by tailoring a surfactant system to other ingredients of the formulation while using decreasing percentages by weight of the propellant and eliminating the vapor tap from the valve. The aerosol products can be flying insects insecticides, room fogger insecticides and air sanitizers. The functional ingredient provides a scent, or insecticidal, germicidal or other function. Examples disclosed include water, a corrosion inhibitor, perfume oil, surfactant(s) and a hydrocarbon propellant.

U.S. Patent Application Publication No. 2003/0005522 A1; and U.S. Pat. Nos. 6,451,065; 6,248,135; 6,077,318, and 5,670,475 disclose an aqueous composition for reducing malodor impression including perfume and an aqueous carrier and optionally a solubilizing aid, cyclodextrin and a metallic salt. The solubilizing aid is to solubilize any excess organic materials, in particular the perfume and other optional ingredients added, such as an insect repelling agent. A suitable solubilizing aid is a surfactant, which can be nonionic, cationic, amphoteric, zwitterionic or mixtures thereof. Anionic surfactants are stated to not be preferred because they form water-insoluble salts with metal ions of metallic salts. The composition can be dispensed from a spray dispenser which may be an aerosol using a propellant such as compressed air.

U.S. Pat. Nos. 5,734,029; 5,266,690; 5,449,763; 5,859, 218, and 5,962,399 disclose alkylpolyglycoside compositions having enhanced surfactant properties and containing mixtures of alkylpolyglycosides of differing alkyl chain lengths, varying degrees of polymerization and surfactant properties. The surfactant alkylpolyglycosides are stated to be useful in personal care, cosmetic, detergent, household and industrial uses. The alkylpolyglycoside mixture is stated to have improved critical micelle concentration (CMC) and interfacial tension (IFT) properties which are useful in emulsification and solubilization.

U.S. Pat. No. 6,729,559 B2 discloses a rotatable aerosol product including a container holding an aerosol composition. The aerosol composition is a concentrate (a liquid containing an effective ingredient) and a propellant. The effective ingredient can be an insecticide or fragrance. The propellant can be a compressed gas such as carbon dioxide, nitrogen, nitrogen suboxide or air. The concentrate may be a spray foam containing a foaming agent such as a surfactant.

U.S. Patent Application Publication No. 2005/0124512 A1 discloses an air and fabric freshener that may contain a perfume and a compressed gas, such as air. The perfume ingredients and any malodor counteractant ingredients can include any suitable percentage and the balance can be a carrier and any optional ingredient such as surfactants.

U.S. Pat. Nos. 5,538,978; 5,494,912, and 5,527,803 disclose purine nucleoside phosphorylase inhibitors. These compounds can be administered as injectable dosages of the compound in a physiologically acceptable diluent. The diluent may be a surfactant, which can be a single component or a mixture, such as high molecular weight adducts of ethylene oxide with a hydrophobic base. The compound can also be administered as an aerosol or spray composition. The spray composition can also contain a surfactant and be applied by means of a propellant under pressure or by means of a compressible plastic spray bottle, nebulizer or atomizer without the use of a gaseous propellant.

European Patent Application No. 0 488 668 A1 discloses a herbicide-containing liquid including a surfactant. The surfactant is to provide foaming and can be cationic, anionic, nonionic, or amphoteric. Diluents to dissolve or suspend the herbicide and surfactant can also be used, such as water, alcohol, ethylene glycol and glycol ethers. The liquid can be applied as an aerosol. The herbicide, surfactant and diluent will be enclosed in an aerosol container together with a propellant, such as a compressed gas (e.g., carbon dioxide, nitrogen gas, nitrous oxide and air).

U.S. Pat. No. 5,489,433 discloses an insecticide composition including hydroxy acyclic acid (as the active) and any ionic or nonionic surfactant. The composition can be delivered in aerosol form. The purpose of the surfactant is stated to be to reduce the surface tension of the insecticidal composition so that when the composition is applied to the body of an insect, the penetration of the hydroxy acyclic acid into the insect's nervous system is facilitated so as to disrupt normal respiratory function of the insect and thereby suffocate the insect.

U.S. Pat. No. 3,829,578 discloses an active antiviral compound which is useful with conventional pharmaceutical carriers, e.g., water, with or without the addition of a surfactant. The active compound can be packaged as an aerosol with a gaseous or liquefied propellant, e.g., carbon dioxide, with the usual adjuvants such as solvents or wetting agents. Typical surface active ingredients which can be used include high molecular weight alkyl polyglycol ethers.

U.S. Patent Application Publication No. 2005/0192197 A1 discloses a peroxycarboxylic acid for reducing a population of microorganisms. Various solubilizers can be used with the acid, including various surfactants. A foaming composition is described which includes the acid compound and foaming surfactants, such as alcohol ethoxylates and alkyl ether sulfates. At the time of use, compressed air can be injected into the mixture.

U.S. Patent Application Publication No. 2005/0165042 A1 discloses an active heterocyclic compound which may be administered by injection. The composition to be injected can contain a nonionic surfactant in conjunction with the heterocyclic compound. The surfactant can be a single component.

U.S. Patent Application Publication No. 2005/0089540 A1 discloses a composition for application to surfaces for providing controlled release of a microencapsulated active ingredient, such as a perfume. The composition can include an aerosol propellant, such as compressed air. In addition to the perfume and propellant, the composition can include a stabilizer, such as isopropyl myristate, a dispersant and an aqueous carrier. The dispersant serves to suspend the microencapsules in the composition. The composition can optionally include a surfactant or a mixture of surfactants.

The above-described compositions have various shortcomings which are addressed by the present invention.

SUMMARY OF THE INVENTION

The present invention relates to the inclusion of a single surfactant selected from specified surfactants in various compositions to dissolve or disperse water-insoluble components of the compositions to provide VOC-free compressed gas aerosol compositions. The compositions of the invention comprise one or more water-insoluble components, a surfactant and water. The water-insoluble component(s) preferably are active agent(s), such as fragrance(s) and/or insecticide(s), which are water-insoluble or contain a water-insoluble component. Since the active agent is water-insoluble, generally, a solvent or a mixture of surfactants is required to dissolve or disperse the active agent. However, the present invention comprises the inclusion of a single surfactant in the absence of a solvent to dissolve or disperse the water-insoluble component(s), e.g., fragrance or insecticide, and to provide a homogenous blend in water. The surfactant of the invention is an anionic surfactant or a nonionic surfactant which produces a stable compressed gas aerosol emulsion. Cationic and zwitterionic surfactants do not provide a stable compressed gas aerosol emulsion in accordance with the present invention.

Combinations of different surfactant groups and single surfactants, usually nonionic and/or anionic surfactants, can create stable emulsions. As such, surfactants are recognized generally as a solubilizing aid or agent. However, aerosol compositions have generally included another ingredient in addition to a surfactant, such as an emulsifier, solvent or solubilizing agent. In contrast, the present invention uses a sole anionic or nonionic surfactant as further detailed below for dissolving or dispersing water-insoluble components, such as active agents, e.g. fragrances and/or insecticides.

The anionic and nonionic surfactants of the invention for dissolving or dispersing one or more water-insoluble component(s), preferably fragrance(s), are nonionic alkylpolyglycosides (e.g., APG® 325 NK, from Cognis-Care Chemicals, Cincinnati, Ohio); nonionic coco-glucoside, i.e., a $C_8$-$C_{16}$ alkylpolyglycoside (e.g., Glucopon® 425 N, from Cognis-Care Chemicals, Cincinnati, Ohio); nonionic alkylene oxide extended chain alkypolyglycosides (APG) (e.g., ethylene oxide or propylene oxide APG); anionic sodium lauryl ether sulfate (SLES), nonionic $C_{13}$-$C_{15}$ oxoalcohol ethoxylate with 8 ethylene oxides (EO), i.e., $C_{13}$-$C_{15}$ ethoxylated fatty alcohol (e.g., Lutensol® AO8, from BASF Aktiengesellschaft, Germany), nonionic $C_{12}$-$C_{14}$ secondary alcohol ethoxylates (e.g., Tergitol® 15-S-7 and Tergitol® 15-S-12, from Dow Chemical Co.), nonionic polyethylene glycol (PEG) hydrogenated castor oil (e.g. Tagat® CH-60 (solid PEG-60 hydrogenated castor oil) and Tagat® CH-40 (solid PEG-40 hydrogenated castor oil) from Goldschmidt Chemical Corp.), nonionic polyglyceryl-10 laurate (e.g. Dermofeel® G10L from Kinetik Technologies, Hazlet, N.J.), and nonionic polyglyceryl-6 caprylate (e.g. Dermofeel® G6CY from Kinetik Technologies). $C_{13}$-$C_{15}$ ethoxylated fatty alcohols (e.g., Lutenosol® AO8), $C_{12}$-$C_{14}$ secondary alcohol ethoxylates (e.g. Tergitol® 15-S-12 and 15-S-7), ethoxylated castor oil (e.g. Tagat® CH-60 and Tagat® CH-40), polyglyceryl-10 laurate and polyglyceryl-6 caprylate (e.g. Dermofeel® G10L and G6CY respectively) are also preferred for dissolving or dispersing insecticides.

BRIEF DESCRIPTION OF THE DRAWINGS

Referring to the drawings:

The sole FIGURE is a graph showing the dynamic surface tension plot for cloudy versus clear emulsions in accordance with the invention.

DETAILED DESCRIPTION OF THE PREFERRED EMBODIMENTS

The present invention relates to the inclusion of a single surfactant, which is selected from specified surfactants, in compositions to dissolve or disperse one or more water-insoluble component(s), e.g., active agent(s) of the compositions, to provide VOC-free compressed gas aerosol compositions. The compositions of the invention comprise one or more water-insoluble components, a surfactant and water. The water-insoluble component(s) is/are preferably active agent(s) such as fragrance(s) and/or insecticide(s) which are or contain water-insoluble components. Due to the water-insoluble nature of the components, a solvent or a mixture of surfactants has in the past been required to dissolve or disperse the water-insoluble component. However, the present invention comprises inclusion of a single surfactant in the absence of a solvent to dissolve or disperse water-soluble components, such as an active agent(s), e.g., fragrance(s) and/or insecticide(s), and to provide a homogenous blend in water. The surfactant is an anionic surfactant or a nonionic surfactant which produces a stable compressed gas aerosol emulsion. Cationic and zwitterionic surfactants do not provide a stable compressed gas aerosol emulsion in accordance with the present invention.

Combinations of different surfactant groups and single surfactants, usually nonionic and/or anionic surfactants, create stable emulsions. As such, surfactants are recognized generally as a solubilizing aid or agent in liquid compositions. However, aerosol compositions have required another ingredient in addition to a surfactant, such as an emulsifier, solvent or solubilizing agent, to create a stable emulsion. The present invention provides a stable emulsion without the inclusion of a solvent through the inclusion of a sole anionic or nonionic surfactant as further detailed herein, for use with water-insoluble components, e.g. active agents such as fragrances and/or insecticides.

The anionic and nonionic surfactants of the invention for dissolving or dispersing a water-insoluble component, and preferably suitable for fragrances, are nonionic alkylpolyglycosides (e.g., APG® 325 NK, from Cognis-Care Chemicals, Cincinnati, Ohio); nonionic coco-glucoside, i.e., a $C_8$-$C_{16}$ alkylpolyglycoside (e.g., Glucopon® 425 N, from Cognis-Care Chemicals, Cincinnati, Ohio); alkylene oxide extended chain alkypolyglycosides (APG) (e.g. ethylene oxide APG, propylene oxide APG); anionic sodium lauryl ether sulfate (SLES), nonionic $C_{13}$-$C_{15}$ oxoalcohol ethoxylate with 8 ethylene oxides (EO), i.e., $C_{13}$-$C_{15}$ ethoxylated fatty alcohol (e.g., Lutensol® AO8, from BASF Aktiengesellschaft, Germany), nonionic $C_{12}$-$C_{14}$ secondary alcohol ethoxylates (e.g., Tergitol® 15-S-7 and Tergitol® 15-S-12, from Dow Chemical Co.), nonionic polyethylene glycol (PEG) hydrogenated castor oil (e.g. Tagat® CH-60 (solid PEG-60 hydrogenated castor oil) and Tagat® CH-40 (solid PEG-40 hydrogenated castor oil) from Goldschmidt Chemical Corp.), nonionic polyglyceryl-10 laurate (e.g. Dermofeel® G10L from Kinetik Technologies, Hazlet, N.J.), and nonionic polyglyceryl-6 caprylate (e.g. Dermofeel® G6CY from Kinetik Technologies). $C_{13}$-$C_{15}$ ethoxylated fatty alcohols (e.g., Lutenosol® AO8), $C_{12}$-$C_{14}$ secondary alcohol ethoxylates (e.g. Tergitol® 15-S-12 and 15-S-7), ethoxylated castor oil (e.g. Tagat® CH-60 and Tagat® CH-40), polyglyceryl-10 laurate and polyglyceryl-6 caprylate (e.g., Dermofeel® G10L and G6CY, respectively) are also preferred for dissolving or dispersing water-insoluble insecticides.

In accordance with the invention, various fragrance oils, insecticide additives and surfactants were tested as described hereafter. The surfactants analyzed included anionic, cationic, zwitterionic and nonionic surfactants.

Twenty fragrances, which are water-insoluble or contain a water-insoluble component, were used in the tests described below. Each fragrance sample was of a different fragrance compound. The fragrances are commercially available and were made by different fragrance manufacturers, i.e., Takasago, Quest and International Flavors and Fragrances.

Table 1 sets forth various insecticide additives and the physical state thereof which were used in the tests described herein.

TABLE 1

Insect additives and physical state

| Chemical Name | Physical State |
| --- | --- |
| Sample 1 - Cyfluthrin | Solid |
| Sample 2 - Propoxin | Powder |
| Sample 3 - MGA 264 | Liquid |
| Sample 4 - *Pyrethrum* Extract | Liquid |
| Sample 5 - Direct Blue 86 | Powder |
| Sample 6 - Permethrin | Crystalline |
| Sample 7 - Cypermethrin | Resin |
| Sample 8 - Imiprothrin | Liquid |
| Sample 9 - Quest Q-9633 | Liquid |
| Sample 10 - Neo-Pynamin | Powder |
| Sample 11 - Sumithrin | Liquid |
| Sample 12 - Pynamin Forte | Liquid |
| Sample 13 - IFF 2178 | Liquid |

Cyfluthrin is α-cyano-3-phenoxy-4-fluorobenzyl-2,2-dimethyl-3(2,2-dichlorovinyl)cyclopropanecarboxylate, from Nanjing Agrovance Chemical Industry Ltd.

MGA 264 is a melengestrol acetate.

Pyrethrum Extract is a natural extract from chrisantemum cinerariifolium flower heads, from AJE GmbH.

Permethrin is a 3-(2,2-Dichloroethenyl)-2,2-dimethylcyclopropanecarboxylic acid (3-phenoxyphenyl)methyl ester; i.e., a 3-phenoxy benzyl (1RS)-cis,trans-3-(2,2 dichlorovinyl)-2,2 dimethyl-cyclopropane carboxylate.

Cypermethrin is a cyano(3-phenoxyphenyl)methyl 3-(2,2-dichloroethenyl)-2,2-dimethylcyclopropane-carboxylate, from Nanjing Agrovance Chemical Industry Ltd.

Imiprothrin is a [2,5-dioxo-3-(2-propynyl)-1-imidazolidinyl]methyl (1R)-2,2-dimethyl-3-(2-methyl-1-propenyl)cyclopropanecarboxylate.

Quest Q-9633 is a formulated mixture of a water conditioning agent and activator designed to enhance pesticide performance by modifying factors such as pH and hard water, from Helena Chemical Co.

Neopynamin is a (1,3,4,5,6,7-hexahydro-1,3-dioxo-2H-isoindol-2-yl)methyl 2,2-dimethyl-3-(2-methyl-1-propenyl)-cyclopropanecarboxylate.

Sumithrin is a 3-phenoxybenzyl 2-dimethyl-3-(methylpropenyl)cyclopropanecarboxylate.

Pynamin Forte is a (1R)-cis,trans-chrysanthemic acid, ester with (RS)-allethrolone.

IFF 2178 is manufactured by International Flavors and Fragrances.

Table 2 sets forth a list of surfactants used in the tests described herein.

TABLE 2

Surfactant Names and Class

| Surfactant Name | Class |
| --- | --- |
| 1 - Alkylbenzene sulfonic acid (linear) | Anionic |
| 2 - Sodium lauryl ether sulfate (SLES) | |
| 3 - Cetrimonium chloride | Cationic |
| 4 - Cocoamidopropyl betaine | Zwitterionic |

TABLE 2-continued

Surfactant Names and Class

| Surfactant Name | Class |
|---|---|
| 5 - Lauramine oxide | |
| 6 - $C_{13}$-$C_{15}$ oxoalcohol ethoxylate with 8 EO; $C_{13}$-$C_{15}$ ethoxylated fatty alcohol | Nonionic |
| 7 - $C_{13}$-$C_{15}$ oxoalcohol ethoxylate with 8 EO; $C_{13}$-$C_{15}$ ethoxylated fatty alcohol | |
| 8 - An ethoxylated fatty alcohol | |
| 9 - fatty alcohol $C_{12}$-$C_{14}$ EO/PO derivative surfactant | |
| 10 - fatty alcohol $C_{12}$-$C_{14}$ EO/PO derivative surfactant | |
| 11 - ST-15 | |
| 12 - Coco-glucoside ($C_8$-$C_{16}$ alkyl polyglycoside) | |
| 13 - alkylpolyglycoside based on synthetic $C_9$-$C_{11}$ fatty alcohol | |
| 14 - Polymeric surfactant #1 | |
| 15 - Polymeric surfactant #2 | |

Specific examples corresponding to the numbers above include:
1 - Biosoft ®, from Stepan Co., Northfield, Illinois
3 - Ammonyx ® CETAC, from Stepan Co., Northfield, Illinois
4 - Lonzaine ® CO, from Lonza Inc., Fair Lawn, New Jersey
5 - Ammonyx ® LO, from Stepan Co., Northfield, Illinois
6 - Lutensol ® A08, from BASF Aktiengesellschaft, Germany
7 - Plurafac ® A08, from BASF Aktiengesellschaft, Germany
8 - Plurafac ® A037, from BASF Aktiengesellschaft, Germany
9 - Dehypon ® LS 36, from Cognis - Care Chemicals, Cincinnati, Ohio
10 - Dehyon ® LS 54, from Cognis - Care Chemicals, Cincinnati, Ohio
11 - ST-15
12 - Glucopon ® 425 N, from Cognis - Care Chemicals, Cincinnati, Ohio
13 - APG ® 325 NK, from Cognis - Care Chemicals, Cincinnati, Ohio
14 - Hypermer ® 70/Atlas ® G5000, from Uniqema, The Netherlands
15 - Hypermer ® B246SF/Atlas ® G5000, from Uniqema, The Netherlands

EXPERIMENTAL PROCEDURE

Small-Scale Test: Fragrance Oils

Fragrances of varying aromatic backgrounds were selected and mixed in small-scale samples to determine their solubility using the varying surfactants. The surfactant to fragrance ratio was tested at high and low levels, and with or without a solubilizer. Table 3 shows a layout for small-scale fragrance oil sample formulations with one surfactant, one fragrance, optionally, propylene glycol present as a solubilizer, and water. Table 3 also shows the ratio of parts of each component in each of samples 1-5. This pattern was completed for each of the predetermined fragrances and each of the surfactants. Samples were made in 20 milliliter vials. The fragrance, surfactant and optional solubilizer, e.g., propylene glycol, were first mixed in the vials and then deionizied water was added.

TABLE 3

Small-scale fragrance oil sample formulations Parts

| | Fragrance | Surfactant | Propylene Glycol | Deionized Water |
|---|---|---|---|---|
| Sample 1 | 1 | 2 | 0 | 100 |
| Sample 2 | 1 | 5 | 0 | 100 |
| Sample 3 | 1 | 2 | 0.02 | 100 |
| Sample 4 | 1 | 2 | 1 | 100 |
| Sample 5 | 1 | 5 | 0.02 | 100 |

Once made, the samples were shaken and observed to determine if a stable solution or emulsion formed. If the system was an emulsion, the time was recorded when the emulsion broke. The surfactants used for dissolving dispersing fragrances were (1) the nonionic alkylpolyglycoside based on synthetic $C_9$-$C_{11}$ fatty alcohols, i.e., APG® 325 NK; (2) the nonionic coco-glucoside $C_8$-$C_{16}$ alkylpolyglycoside, i.e., Glucopon® 425 N; (3) the anionic sodium lauryl ether sulfate (SLES), and (4) the nonionic $C_{13}$-$C_{15}$ oxoalcohol ethoxylate with 8 ethyleneoxides (EO), i.e., Lutensol® AO8. These surfactants are discussed in greater detail hereafter.

Large-Scale Test: Fragrance Oils

Larger samples were made in glass aerosol containers in order to view the solutions. The four surfactants of the small-scale test detailed above were used with each of the twenty fragrances. Nitrogen was added to the samples to place them under pressure. The samples were then ranked visually and a preferred sample was chosen.

Clear Versus Cloudy Emulsions

With the preferred sample chosen, spray characteristics were taken to determine if there was a difference between using a cloudy emulsion versus a clear emulsion. Certain fragrance oils were easier to put into solution than other fragrance oils, thus resulting in both clear and cloudy solutions for the same surfactant. With a "no-difference" result from these comparisons, either a cloudy or a clear solution could be used, as long as the solution is homogeneous, and the surfactant levels can therefore be minimized. In order to test this, a fragrance oil known in the art to be difficult to place into solution and a fragrance oil known in the art to be easy to place into solution in comparison were used in a ratio set-up. These ratios are shown in Table 4. These formulations were then placed into 200/700 cans and pressurized to around 95 psi using nitrogen gas.

TABLE 4

Ratios for emulsion clarity study

| | Ratio | Description |
|---|---|---|
| A | 9:01 | Difficult Oil:Clear at lowest load |
| B | 9:01 | Easy Oil:Clear at same load as A |
| C | 1.4:1 | Easy Oil:Clear at lowest load |
| D | 1:01 | Easy Oil:Cloudy at highest load |
| E | 1:01 | Difficult Oil:Cloudy at same load as D |

Thereafter, the following parameters were analyzed to test parity, particle size, spray rate, span, concentration, obscuration, retention and dynamic surface tension of the samples. Particle size, span, concentration and obscuration were determined using a particle sizer, in particular the Malvern particle sizer. Spray rate and retention were measured using known spray and weigh techniques. Dynamic surface tension was determined using a bubble pressure tensiometer.

RESULTS

Small-Scale Test: Fragrance Oils

Results from the small-scale fragrance formulations test are shown in Table 5. In Table 5, an "S" indicates that the resulting emulsions were soluble, staying in solution for over 24 hours. An "I" indicates that the oil was insoluble. An "E/t" indicates that the solution did not form an emulsion, with the "t" indicating the amount of time it took for the emulsion to break (in hours).

TABLE 5

| | Fragrance S/C | Fragrance T/M | Fragrance R/A | Fragrance L/S | Fragrance S/F | Fragrance M/S | Fragrance R/S |
|---|---|---|---|---|---|---|---|
| $C_{13}$-$C_{15}$ oxoalcohol ethoxylate with 8 EO; $C_{13}$-$C_{15}$ ethoxylated alcohol (Lutensol ® A08) | S | S | S | S | S | S | S |
| An ethoxylated fatty alcohol (Plurafac ® A037) | E/0.5 | E/0.5 | E/0.5 | E/0.5 | E/0.5 | E/0.5 | E/0.5 |
| Sorbitan Monooleate (Span ® 80) | E/1.5 | E/1.5 | E/1.5 | E/1.5 | E/1.5 | E/1.5 | E/1.5 |
| Sodium Lauryl Ether Sulfate (SLES) | S | S | S | E/24 | E/24 | S | S |
| Fatty alcohol $C_{12}$-$C_{14}$ EO/PO derivative surfactant (Dehypon ® LS-36) | E/3.5 | E/3.5 | E/3.5 | E/2.5 | E/5.5 | E/5.5 | E/3.5 |
| Fatty alcohol $C_{12}$-$C_{14}$ EO/PO derivative (Dehypon ® LS-54) | S | E/4.5 | E/4.5 | E/5.5 | E/4.5 | E/24 | E/3.5 |
| ST-15 | S | S | E/24 | E/1.5 | E/4.5 | E/24 | S |
| Coco-glucoside; $C_8$-$C_{16}$ alkyl polyglycoside (Glucopon ® 425 N) | S | S | E/24 | E/24 | E/24 | S | E/24 |
| Alkylpoly-glycoside based on synthetic $C_9$-$C_{11}$ fatty alcohol (APG ® 325 NK) | S | S | S | S | S | E/24 | E/24 |
| Cocoamido-propyl betaine (Lonzaine ® CO) | S | E/5.5 | S | S | S | S | S |
| Cetrimonium chloride (Ammonyx ® CETAC) | S | E/6 | E/4 | E/4 | E/4 | E/4 | E/3 |
| Lauramine oxide (Ammonyx ® LO) | S | E/4 | S | S | E/5 | E/24 | E/4 |
| Alkylbenzene sulfonic acid (linear) (Biosoft ®) | S | E/4 | E/5 | E/5 | E/4 | E/5 | E/4 |

S—Soluble
I—Insoluble
E/t - Emulsion/time (hours) to break emulsion

As shown in Table 5, none of the surfactant/fragrance combinations resulted in an insoluble solution. However, samples suitable for use are those that are completely soluble across the board, i.e., the surfactant with each fragrance forms a soluble composition, or samples that kept an emulsion for at least 24 hours, i.e., $C_{13}$-$C_{15}$ oxoalcohol ethoxylate with 8 EO ($C_{13}$-$C_{15}$ ethoxylated fatty alcohol, Lutensol® AO8); sodium lauryl ether sulfate (SLES); coco-glucoside ($C_8$-$C_{16}$ alkylpolyglycoside, Glucopon® 425 N); alkylpolyglycoside based on synthetic $C_9$-$C_{11}$ fatty alcohols (APG® 325 NK).

$C_{13}$-$C_{15}$ oxoalcohol ethoxylate with 8 EO, i.e., $C_{13}$-$C_{15}$ ethoxylated fatty alcohol, e.g., Lutensol® AO8; sodium lauryl ether sulfate (SLES); coco-glucoside, i.e., $C_8$-$C_{16}$ alkyl polyglycoside, e.g., Glucopon® 425 N, and alkylpolyglycoside based on synthetic $C_9$-$C_{11}$ fatty alcohols, e.g., APG® 325 NK, were also used in a large-scale test. These surfactants were selected at their optimal ratios determined from the small-scale samples. Sodium lauryl ether sulfate and coco-glucoside, i.e., Glucopon® 425 N, were mixed in a 2:1 ratio with the fragrance oils, while the optimal ratio for the $C_{13}$-$C_{15}$ oxoalcohol ethoxylate with 8 EO, e.g., Lutensol® AO8, and alkylpolyglycoside based on synthetic $C_9$-$C_{11}$ fatty alcohols, e.g., APG® 325 NK, were mixed at a 5:1 ratio with the fragrance oils. Examples 1 and 2 detailed below describe the formulations used to mix these solutions for the large-scale test.

The following examples are illustrative and not intended to limit the scope of the invention.

EXAMPLE 1

2:1 Surfactant to Fragrance Oil Under Nitrogen Gas 0.88 grams fragrance oil and 1.76 grams surfactant were added to a 140 milliliter glass aerosol bottle and were mixed. To this solution, 87.37 grams of deionized water was added and the resulting solution was then mixed. A valve standard for this size bottle was crimped thereon and approximately 0.2 grams nitrogen gas was added to bring the overall pressure of the solution to 60 psi.

EXAMPLE 2

5:1 Surfactant to Fragrance Oil Under Nitrogen Gas 0.88 grams fragrance oil and 4.26 grams surfactant were added to a 140 milliliter glass aerosol bottle and were mixed. To this solution, 84.87 grams deionized water was added and the resulting solution was then mixed. A valve standard for this size bottle was crimped thereon, and approximately 0.2 grams nitrogen gas was added to bring the overall pressure of the solution to 60 psi.

Large-Scale Test: Fragrance Oils

All twenty fragrances were used in a qualitative test on the four surfactants identified above. Table 6 shows how each of these four surfactants ranked in accordance with each of the fragrance oils. A numeric system was established to use in the ranking, since all of the formulations created mostly stable emulsions. A "1" indicates a crystal-clear solution. A "2" indicates that the emulsion was slightly cloudy. A "3" indicates that the emulsion is stable but cloudy. A "4" indicates that there is some separation. A "5" indicates an unstable emulsion. These rankings were assigned after the emulsions were allowed to sit for 48 hours.

TABLE 6

Stability results from glass aerosol test for fragrances after 48 hours

| | Alkylpolyglycoside based on synthetic $C_9$-$C_{11}$ fatty alcohols (APG® 325 NK) | Coco-glucoside; $C_8$-$C_{16}$ alkyl polyglycoside (Glucopon® 425 N) | $C_{13}$-$C_{15}$ oxoalcohol ethoxylate with 8 EO; $C_{13}$-$C_{15}$ ethoxylated fatty alcohol (Lutensol® A08) | Sodium Lauryl Ether Sulfate |
|---|---|---|---|---|
| Fragrance S/C | 1 | 1 | 1 | 1 |
| Fragrance C/G | 2 | 2 | 5 | 3 |
| Fragrance S/F | 2 | 2 | 3 | 3 |
| Fragrance T/M | 2 | 3 | 2 | 3 |
| Fragrance R/A | 1 | 2 | 2 | 3 |
| Fragrance R/S | 2 | 4 | 2 | 3 |
| Fragrance S/S | 2 | 3 | 3 | 4 |
| Fragrance L/S | 2 | 2 | 3 | 3 |
| Fragrance M/S | 2 | 2 | 2 | 3 |
| Fragrance C/L | 1 | 2 | 3 | 3 |
| Fragrance M/M | 2 | 2 | 3 | 4 |
| Fragrance G | 1 | 2 | 3 | 3 |
| Fragrance F/V | 1 | 1 | 1 | 1 |
| Fragrance P/F | 1 | 2 | 1 | 1 |
| Fragrance N | 2 | 2 | 1 | 1 |
| Fragrance H/B | 1 | 4 | 1 | 2 |
| Fragrance L/M | 2 | 2 | 3 | 4 |
| Fragrance C/S | 2 | 2 | 5 | 1 |
| Fragrance M/B | 2 | 3 | 3 | 3 |
| Fragrance B/G | 2 | 3 | 3 | 3 |
| Averages | 1.65 | 2.3 | 2.5 | 2.6 |

1 - crystal-clear solution
2 - emulsion slightly cloudy
3 - emulsion stable, but cloudy
4 - some separation
5 - unstable emulsion From the results shown in Table 6, it can be seen that all the formulations formed good, stable emulsions. Alkylpolyglycoside based on synthetic $C_9$-$C_{11}$ fatty alcohols, e.g., APG® 325 NK was shown to form the highest number of clear solutions with the least amount of any type of separation. Coco-glucoside, i.e., $C_8$-$C_{16}$ alkyl polyglycoside, Glucopon® 425 N, and sodium lauryl ether sulfate, each performed at good levels for application in the present invention.

The clarity of the emulsion affecting the resulting spray was also determined. All of the emulsions formed were stable emulsions, but some were crystal-clear emulsions while others were cloudy in nature. To show the non-effect thereof when used in accordance with the invention, samples were made at varying surfactant ratios to achieve clear and cloudy solutions with different fragrances at the same surfactant levels.

Parity Between Cloudy and Clear Emulsions

To show that a viable surfactant package is provided, parity was shown to exist between the clear and cloudy solutions. Tables 7A and 7B show the spray characteristics obtained from spraying down the sample formulations previously described in Table 4, using alkylpolyglycoside based on synthetic $C_9$-$C_{11}$ fatty alcohols, e.g., APG® 325 NK, as the surfactant. These measurements were recorded starting from the initial fill weight (Table 7A) and then later when the samples were sprayed down to an equal weight to simulate "late in life" situations (Table 7B). Two samples of each were run and averaged to ensure consistency.

Tables 7A and 7B: Spray Characteristics for Cloudy Versus Clear Emulsions

TABLE 7A

| Initial Readings Sample # | D(3, 2) Particle Size$^{ave}$ | D(V, 0.5) Particle Size$^{ave}$ | Span$^{ave}$ | Obscuration$^{ave}$ | Conc.$^{ave}$ |
|---|---|---|---|---|---|
| A | 70.43 | 93.73 | 1.11 | 27.28% | 0.075% |
| B | 75.88 | 99.43 | 1.17 | 25.65% | 0.060% |
| C | 77.05 | 94.58 | 3.25 | 26.33% | 0.079% |
| D | 77.73 | 94.33 | 5.40 | 27.10% | 0.080% |
| E | 76.15 | 91.48 | 3.24 | 25.63% | 0.075% |

TABLE 7B

| Late in Life Readings Sample # | D(3, 2) Particle Size$^{ave}$ | D(V, 0.5) Particle Size$^{ave}$ | Span$^{ave}$ | Obscuration$^{ave}$ | Conc.$^{ave}$ | Retention |
|---|---|---|---|---|---|---|
| A | 94.53 | 108.53 | 1.13 | 19.53% | 0.066% | 0.46 |
| B | 91.23 | 111.63 | 1.21 | 20.33% | 0.069% | 0.45 |
| C | 88.80 | 107.85 | 1.08 | 19.40% | 0.064% | 0.34 |
| D | 90.45 | 105.43 | 3.03 | 18.78% | 0.062% | 0.59 |
| E | 91.55 | 103.90 | 5.23 | 18.08% | 0.059% | 0.47 |

Particle size was measured in microns, spray rate was measured in grams per second, retention was measured in grams, and both concentration and obscuration were determined and reported as percentages. The span is the relation between the largest and smallest particle sizes detected by a particle sizer, such as the Malvern particle sizer. Overall particle size is determined as both the volume median diameter (D(V, 0.5)) and the surface area moment mean diameter (D(3,2)). The sole FIGURE displays the surface tensions for each of these solutions.

As shown in the Figure and Tables 7A and 7B, the visual appearance of the emulsion did not have any significant effect on the overall spray characteristics of the aerosol. Therefore, it is possible to maximize the overall formulation to minimize surfactant usage without jeopardizing spray characteristics.

$C_{12}$-$C_{14}$ alcohol ethoxylates with 7EO or 12EO (e.g., Tergitol® 15-S-7 and Tergitol® 15-S-12), PEG-60 hydrogenated castor oil (e.g. Tagat® CH-60), PEG-40 hydrogenated castor oil (e.g. Tagat® CH-40), polyglyceryl-10 laurate (e.g. Dermofeel® G10L), polyglyceryl-6 caprylate (e.g. Dermofeel® G6CY), and alkylpolyglycoside based on synthetic $C_9$-$C_{11}$ fatty alcohols (e.g., APG® 325 NK) are preferred for solubilizing fragrance oils. Once optimized, the preferred ratio is 4:1 surfactant to fragrance oil therefor. Coco-glucoside, i.e., $C_8$-$C_{16}$ alkyl polyglycoside, e.g., Glucopon® 425 N; sodium lauryl ether sulfate, and $C_{13}$-$C_{15}$ oxoalcohol ethoxylate with 8 EO, i.e., $C_{13}$-$C_{15}$ ethoxylated fatty alcohol, e.g., Lutensol® AO8, are also preferred surfactants for forming fragrance oil emulsions. $C_{12}$-$C_{14}$ secondary alcohol ethoxylate with 7EO or 12EO, PEG 60 or PEG 40 hydrogenated castor oil, polyglyceryl-10 laurate, polyglyceryl-6 caprylate, and $C_{13}$-$C_{15}$ oxoalcohol ethoxylate with 8 EO, i.e., $C_{13}$-$C_{15}$ ethoxylated fatty alcohol, e.g., Lutensol® AO8, are preferable for solubilizing insect additives. The preferred, unoptimized ratio therefor is 5:1 surfactant to insect additive.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention.

It is claimed:

1. An aqueous aerosol composition comprising:
   one anionic or nonionic surfactant;
   at least one water-insoluble component;
   a compressed gas propellant; and
   water,
   wherein said one surfactant dissolves or disperses said at least one water-insoluble component, in absence of a solvent or solubilizing agent which is capable of dissolving or dispersing the at least one water-insoluble component and in absence of an additional surfactant, to provide a homogenous blend in water which is a stable compressed gas aerosol emulsion and wherein the composition does not include any cationic or zwitterionic surfactant and does not include any volatile organic propellant or volatile organic solvent compound.

2. The composition of claim 1, wherein said at least one water-insoluble component is a fragrance.

3. The composition of claim 1, wherein said at least one water-insoluble component is an insecticide.

4. The composition of claim 1, wherein said surfactant is sodium lauryl ether sulfate.

5. The composition of claim 1, wherein said surfactant is an alkylpolyglycoside based on $C_9$-$C_{11}$ fatty alcohols.

6. The composition of claim 1, wherein said surfactant is a $C_8$-$C_{16}$ alkylpolyglycoside.

7. The composition of claim 1, wherein the surfactant is a $C_{13}$-$C_{15}$ oxoalcohol ethoxylate with eight ethylene oxides.

8. The composition of claim 1, wherein the surfactant is a $C_{12}$-$C_{14}$ secondary alcohol ethoxylate with 7 ethylene oxides.

9. The composition of claim 1, wherein the surfactant is a $C_{12}$-$C_{14}$ secondary alcohol ethoxylate with 12 ethylene oxides.

10. The composition of claim 1, wherein the surfactant is polyethylene glycol (60) hydrogenated castor oil.

11. The composition of claim 1, wherein the surfactant is polyethylene glycol (40) hydrogenated castor oil.

12. The composition of claim 1, wherein the surfactant is polyglyceryl-10 laurate.

13. The composition of claim 1, wherein the surfactant is polyglyceryl-6 caprylate.

14. The composition of claim 2, wherein said fragrance and said surfactant are present in a fragrance to surfactant ratio of 1:2.

15. The composition of claim 2, wherein said fragrance and said surfactant are present in a fragrance to surfactant ratio of 1:5.

16. The composition of claim 3, wherein said insecticide and said surfactant are present in an insecticide to surfactant ratio of 1:2.

17. The composition of claim 3, wherein said insecticide and said surfactant are present in an insecticide to surfactant ratio of 1:5.

* * * * *